US 9,974,526 B2

(12) United States Patent
Mamiya et al.

(10) Patent No.: US 9,974,526 B2
(45) Date of Patent: May 22, 2018

(54) ULTRASONIC ENDOSCOPE BIOPSY SYSTEM WITH TREATMENT TOOL HAVING VARIOUS RIGIDITY SECTIONS

(71) Applicant: OLYMPUS CORPORATION, Hachioji-shi, Tokyo (JP)

(72) Inventors: Tomohiko Mamiya, Kawasaki (JP); Nozomu Kotake, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days. days.

(21) Appl. No.: 15/374,249

(22) Filed: Dec. 9, 2016

(65) Prior Publication Data

US 2017/0086802 A1 Mar. 30, 2017

Related U.S. Application Data

(63) Continuation of application No. PCT/JP2016/050652, filed on Jan. 12, 2016.

(30) Foreign Application Priority Data

Mar. 26, 2015 (JP) .................................. 2015-063543

(51) Int. Cl.
*A61B 5/00* (2006.01)
*A61B 10/04* (2006.01)
(Continued)

(52) U.S. Cl.
CPC .............. *A61B 10/04* (2013.01); *A61B 1/005* (2013.01); *A61B 1/00137* (2013.01);
(Continued)

(58) Field of Classification Search
CPC ......... A61B 10/04; A61B 1/018; A61B 1/005; A61B 8/12; A61B 1/2736; A61B 5/425; A61B 1/00137; A61B 2010/045
See application file for complete search history.

(56) References Cited

U.S. PATENT DOCUMENTS

| 2007/0249940 A1 | 10/2007 | Kohno |
| 2008/0139960 A1* | 6/2008 | Tonomura ............... A61B 10/04 600/566 |

(Continued)

FOREIGN PATENT DOCUMENTS

| EP | 2 368 499 A1 | 9/2011 |
| JP | 2001-120557 A | 5/2001 |

(Continued)

OTHER PUBLICATIONS

Feb. 9, 2016 International Search Report issued in International Patent Application No. PCT/JP2016/050652.

*Primary Examiner* — Serkan Akar
(74) *Attorney, Agent, or Firm* — Oliff PLC (57) ABSTRACT

A biopsy system includes an endoscope which includes an insertion portion having a channel, and a bendable portion provided in a distal end portion of the insertion portion; a needle tube which includes a distal end region, and a proximal end region having a higher bending rigidity than that of the distal end region; a sheath which can be inserted into the channel and inserted through by the needle tube; an attachment adapter which is provided on a proximal end side of the sheath and is capable of being mounted at the endoscope; and a connection member which connects the distal end region and the proximal end region, wherein the connection member can move within only a range of the insertion portion more proximal than a proximal end of the bendable portion and more distal than a proximal end of a follow-bending region.

7 Claims, 9 Drawing Sheets

(51) Int. Cl.
  *A61B 8/12* (2006.01)
  *A61B 1/018* (2006.01)
  *A61B 1/005* (2006.01)
  *A61B 1/00* (2006.01)
  *A61B 1/273* (2006.01)
  A61M 39/10 (2006.01)
  A61M 25/00 (2006.01)
  A61M 25/10 (2013.01)

(52) U.S. Cl.
  CPC ............ *A61B 1/018* (2013.01); *A61B 1/2736* (2013.01); *A61B 5/425* (2013.01); *A61B 8/12* (2013.01); *A61B 2010/045* (2013.01); *A61M 25/0097* (2013.01); *A61M 25/1025* (2013.01); *A61M 39/10* (2013.01)

(56) References Cited

U.S. PATENT DOCUMENTS

| | | | |
|---|---|---|---|
| 2012/0197119 A1 | 8/2012 | Takachi | |
| 2013/0237879 A1* | 9/2013 | Takeuchi | A61B 8/0841 600/567 |
| 2014/0163371 A1* | 6/2014 | Matsui | A61B 18/24 600/439 |
| 2015/0087994 A1 | 3/2015 | Matsuno et al. | |

FOREIGN PATENT DOCUMENTS

| | | |
|---|---|---|
| JP | 2007-252458 A | 10/2007 |
| JP | 5629043 B1 | 11/2014 |
| WO | 2010/074153 A1 | 7/2010 |

* cited by examiner

ULTRASONIC ENDOSCOPE BIOPSY SYSTEM WITH TREATMENT TOOL HAVING VARIOUS RIGIDITY SECTIONS

This application is a continuation application based on a PCT International Application No. PCT/JP2016/050652, filed on Jan. 12, 2016, whose priority is claimed on Japanese Patent Application No. 2015-063543, filed on Mar. 26, 2015. The contents of both the PCT International Application and the Japanese Patent Application are incorporated herein by reference.

BACKGROUND OF THE INVENTION

Field of the Invention

The present invention relates to a biopsy system and a treatment tool which is suitably used in the biopsy system.

Description of Related Art

In the related art, so-called biopsy that is an inspection method in which a minute quantity of body tissue is collected and is observed with a microscope has been known. In a case of collecting tissue deep inside organs, since it is difficult to perform observation with an optical endoscope, an ultrasonic tomographic image of the organs is acquired by an ultrasonic endoscope or the like, and the tissue is collected by puncturing the organs with a puncture needle having a tubular needle tube while performing ultrasonic observation (for example, refer to Japanese Unexamined Patent Application, First Publication No. 2001-120557).

In the puncture needle, the needle tube is disposed inside a sheath which can be inserted through a treatment tool channel of the ultrasonic endoscope or the like, and an inner surface of the treatment tool channel is configured to be difficult to be damaged by a sharp distal end of the needle tube.

The pancreas is one of target organs for biopsy. Since the pancreas is positioned on a rear side of the gastrointestinal tract, it is possible to collect tissue of the pancreas by causing the puncture needle to protrude from the endoscope that is introduced into the gastrointestinal tract, and thus puncturing the puncture needle into the pancreas through the gastrointestinal tract.

SUMMARY OF THE INVENTION

According to a first aspect of the present invention, a biopsy system includes an endoscope which includes an insertion portion having a channel, and a bendable portion provided in a distal end portion of the insertion portion and capable of being operated to be bent; a needle tube which includes a distal end region, and a proximal end region having a higher bending rigidity than the bending rigidity of the distal end region; a sheath which is capable of being inserted into the channel and inserted through by the needle tube; a connection member which connects the distal end region and the proximal end region; and an attachment adapter which is provided on a proximal end side of the sheath and is capable of being mounted at the endoscope, wherein the connection member is capable of moving within only a range of the insertion portion more proximal than a proximal end of the bendable portion and more distal than a proximal end of a follow-bending region which is capable of being passively bent along a greater curvature of the stomach when a distal end of the insertion portion is positioned at a position of the duodenal bulb, in a state where the sheath is inserted through the channel and the attachment adapter is mounted at the endoscope.

According to a second aspect of the present invention, in the biopsy system according to the first aspect, the proximal end of the follow-bending region may be located in a position 41 centimeters from the distal end of the insertion portion.

According to a third aspect of the present invention, the biopsy system according to the first aspect may further include a needle tube operation portion which advances and retracts the needle tube relative to the sheath, wherein the connection member is capable of moving within the range in accordance with an operation of the needle tube operation portion.

According to a fourth aspect of the present invention, a treatment tool includes a needle tube which includes a distal end region, and a proximal end region having a higher bending rigidity higher than the bending rigidity of the distal end region; a connection member which connects the distal end region and the proximal end region; a sheath which is inserted through by the needle tube; and a needle tube operation portion which advances and retracts the needle tube relative to the sheath, wherein the connection member is capable between a position 8 centimeters from a distal end of the sheath toward a proximal end side of the sheath and a position 40 centimeters from the distal end of the sheath toward the proximal end side of the sheath in accordance with an operation of the needle tube operation portion.

According to a fifth aspect of the present invention, in the treatment tool according to the fourth aspect, the sheath may include a first inner sheath disposed on the distal end side, a second inner sheath disposed more proximal than the first inner sheath and spaced from the first inner sheath, and an outer sheath in which the first inner sheath and the second inner sheath are disposed, an outer diameter of the connection member may be larger than an outer diameter of the distal end region and an outer diameter of the proximal end region, and the connection member may be positioned between a proximal end of the first inner sheath and a distal end of the second inner sheath, and is overlapped with the first inner sheath and the second inner sheath along a radial direction of the first inner sheath and the second inner sheath.

DETAILED DESCRIPTION OF THE INVENTION

Figure 1:
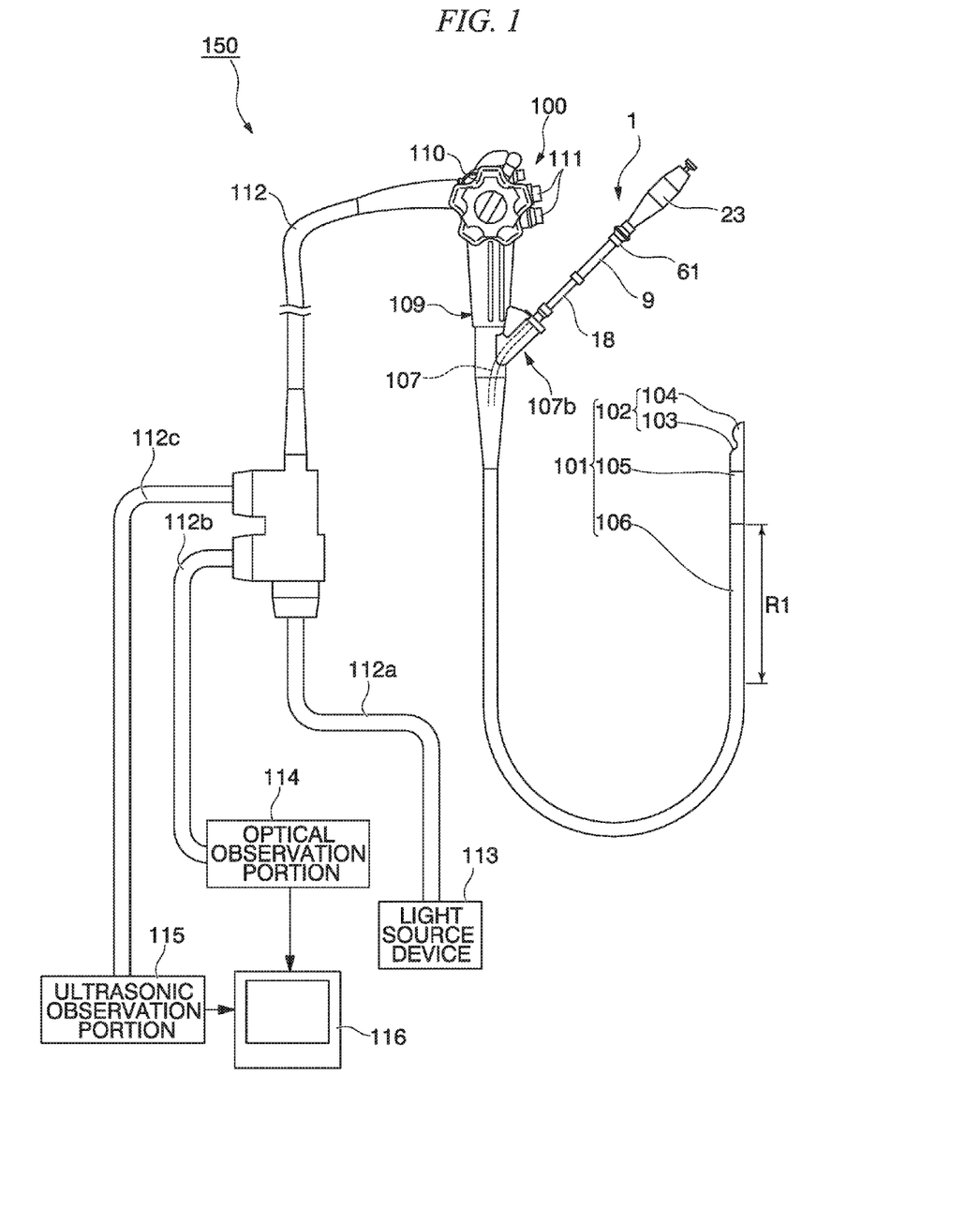
FIG. 1 is a general view of a biopsy system according to an embodiment of the present invention.
Figure 2:
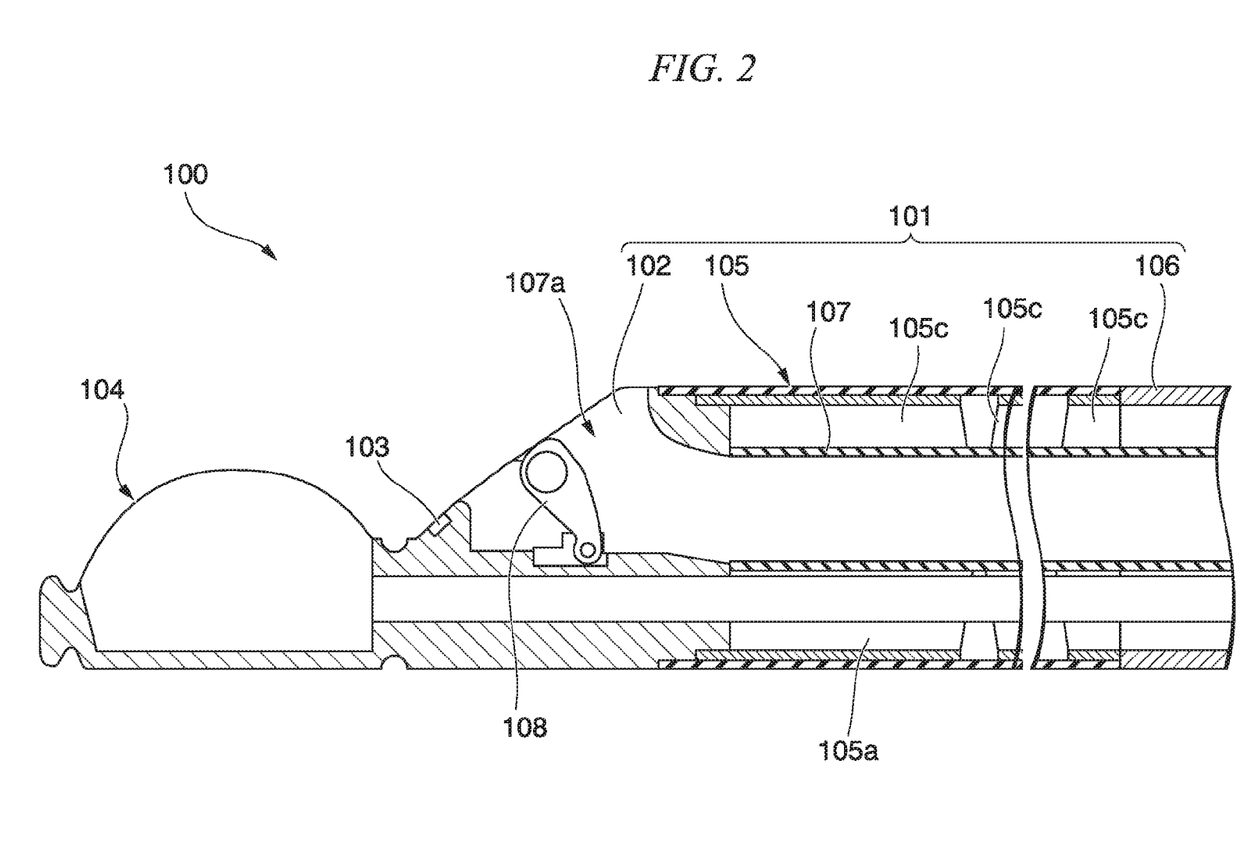
FIG. 2 is a sectional view of a distal end portion of an ultrasonic endoscope in the biopsy system according to the embodiment of the present invention.
Figure 3:
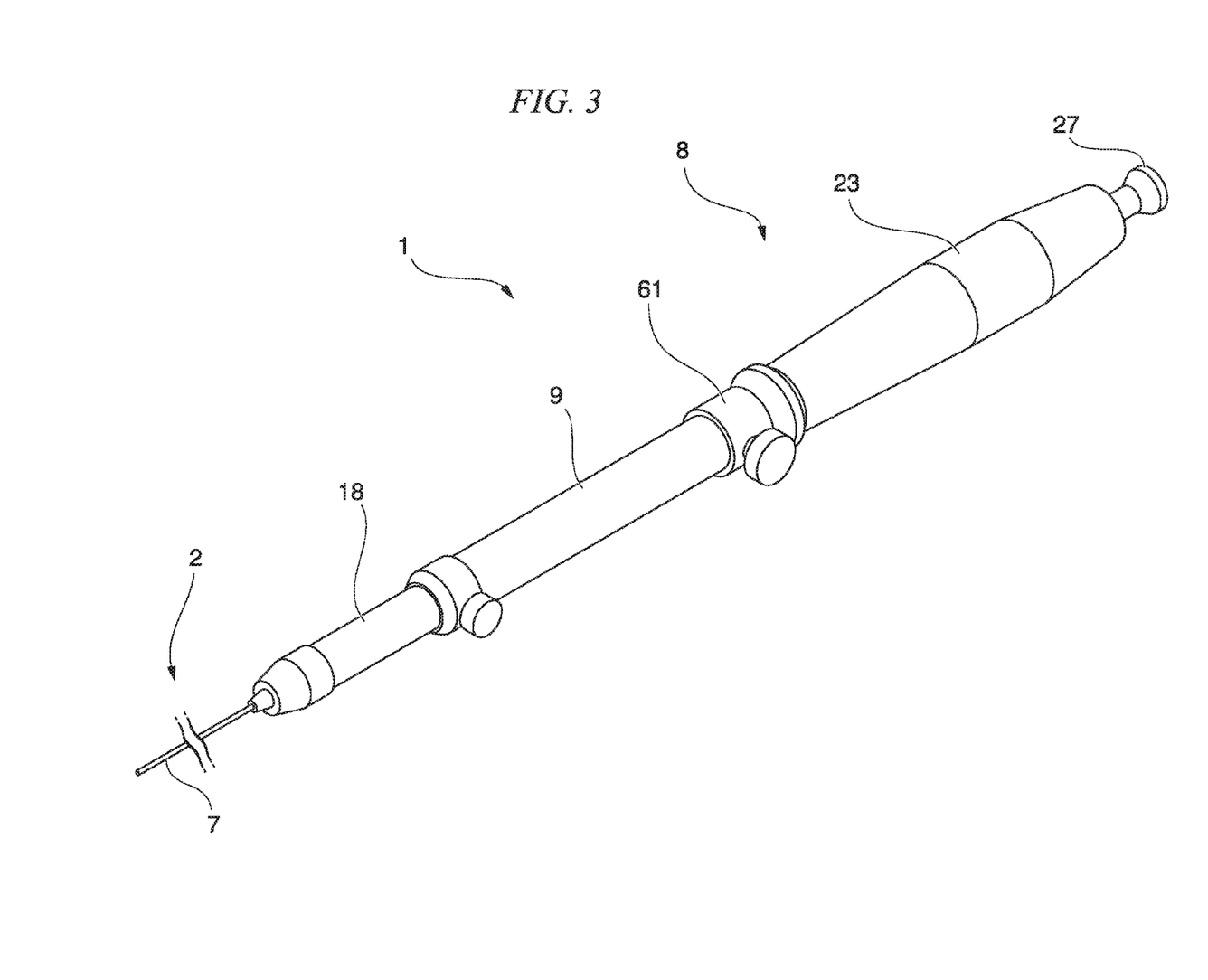
FIG. 3 is a perspective view of a puncture needle for an endoscope according to the embodiment of the present invention.
Figure 4:
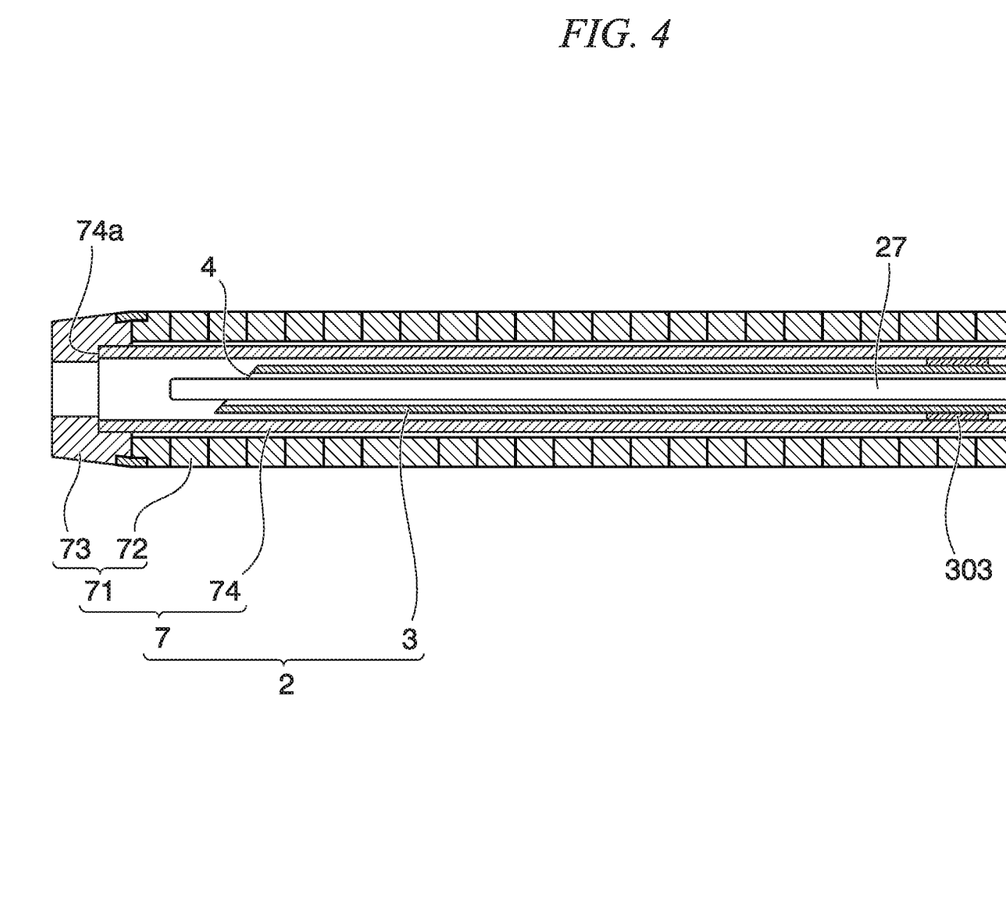
FIG. 4 is a sectional view of a distal end portion of the puncture needle for an endoscope according to the embodiment of the present invention.

An embodiment of the present invention will be described. FIG. 1 is a general view of a biopsy system 150 according to the present embodiment. FIG. 2 is a sectional view of a distal end portion of an ultrasonic endoscope in the biopsy system 150. FIG. 3 is a perspective view of a puncture needle (treatment tool) 1 for an endoscope in the biopsy system 150. FIG. 4 is a sectional view of a distal end portion of the puncture needle 1 for an endoscope.

The biopsy system 150 includes an ultrasonic endoscope 100 and the puncture needle 1 for an endoscope (hereinafter, will be simply referred to as "puncture needle 1").

As shown in FIG. 1, the ultrasonic endoscope 100 includes an insertion portion 101, an operation portion 109, a universal cord 112, a light source device 113, an optical observation portion 114, and an ultrasonic observation portion 115. The insertion portion 101 is configured to be inserted into a body from a distal end. The operation portion 109 is attached to a proximal end of the insertion portion 101. A first end of the universal cord 112 is connected to a side portion of the operation portion 109. The light source device 113 is connected to a second end of the universal cord 112 via a branch cable 112a, the optical observation portion 114 is connected thereto via a branch cable 112b, and the ultrasonic observation portion 115 is connected thereto via a branch cable 112c.

In the insertion portion 101, a rigid distal end portion 102, a bendable portion 105, and a flexible tube portion 106 are provided so as to be arranged in order from the distal end side.

As shown in FIG. 2, the rigid distal end portion 102 includes an optical image-capturing mechanism 103, an ultrasonic scanning mechanism 104, and a raising stand 108. The optical image-capturing mechanism 103 is provided in order to perform an optical observation. The ultrasonic scanning mechanism 104 is provided in order to perform an ultrasonic observation. The raising stand 108 is provided in order to adjust the orientation of the puncture needle 1 inserted through a channel 107 (will be described later).

The optical image-capturing mechanism 103 includes an image-capturing optical system, an image sensor, and various types of configurations (not shown) such as a CPU which controls operation of the image sensor. The visual field of the image-capturing optical system is oriented obliquely forward from the rigid distal end portion 102. The image sensor is configured to be a CCD, a CMOS, or the like detecting an incident image of a subject through the image-capturing optical system.

The ultrasonic scanning mechanism (probe) 104 includes an ultrasonic transducer (not shown) which emits and receives ultrasonic waves. In the ultrasonic scanning mechanism 104, the ultrasonic transducer receives a reflected wave, that is, an ultrasonic wave emitted by the ultrasonic transducer and reflected after hitting an observation target. A signal based on the ultrasonic wave received by the ultrasonic transducer is output to the ultrasonic observation portion 115. The ultrasonic scanning mechanism 104 according to the present embodiment acquires an ultrasonic image of tissue that becomes a biopsy target. In addition, the ultrasonic scanning mechanism 104 is used for acquiring an ultrasonic image of a needle tube 3 of the puncture needle 1 during the technical process of biopsy.

As shown in FIG. 2, the raising stand 108 is a member that changes the orientation of a distal portion of a sheath 7 (refer to FIG. 3) of the puncture needle 1 to a direction intersecting the center line of the insertion portion 101. The raising stand 108 can push the outer surface of the sheath 7 and can cause the sheath 7 to be deformed in a bent state where an operation of pulling a raising wire (not shown) extending to the operation portion 109 is performed through the operation portion 109 (refer to FIG. 6).

The bendable portion 105 is a cylindrical member configured to have multiple cylindrical joints 105c that are interlocked with each other and are arranged in the center line direction of the insertion portion 101. The bendable portion 105 is bent in a predetermined direction when the operation portion 109 performs an operation of pulling an angle wire (not shown) which is fixed to a distal end 105a (refer to FIG. 2) of the bendable portion 105 and extends to the operation portion 109. The bendable portion 105 according to the present embodiment can be bent in two directions along a scanning direction of ultrasonic waves of an ultrasonic scanning mechanism 104. In the present embodiment, a proximal end of the bendable portion 105 is in a position 9 to 10 centimeters from the distal end of the insertion portion 101.

The bending direction of the bendable portion may be four directions without being limited to two directions.

Both the raising stand 108 and the bendable portion 105 are bending property imparting means for causing the puncture needle 1 to be deformed so as to have a bent shape in response to an active bending operation performed by the operation portion 109.

The flexible tube portion 106 is a cylindrical member that is flexibly formed such that the rigid distal end portion 102 can be guided to a desired position inside lumen tissue or inside a body cavity.

Inside each of the bendable portion 105 and the flexible tube portion 106, the channel 107 and a pipe line (not shown) for performing air/water feeding, suctioning, and the like are provided. In the flexible tube portion 106, a range within a predetermined length from the proximal end of the bendable portion 105 is defined as "follow-bending region" in the present invention and will be described later in detail.

As shown in FIGS. 1 and 2, the channel 107 is a tubular portion through which the puncture needle 1 can be inserted.

As shown in FIG. 2, the distal end of the channel 107 is open in the vicinity of the distal end portion of the rigid distal end portion 102. As shown in FIG. 1, the proximal end of the channel 107 is open on a side surface of the distal end side of the operation portion 109. During the process in which the sheath 7 of the puncture needle 1 protrudes from the distal end of the channel 107, the raising stand 108 can come into contact with the outer surface of the sheath 7 of the puncture needle 1. A proximal end mouth piece 107b formed so as to have a flange shape is fixed to the proximal end of the channel 107. The puncture needle 1 which is used together with the ultrasonic endoscope 100 can be fixed to the proximal end mouth piece 107b.

As shown in FIG. 1, the operation portion 109 has an outer surface which is formed so as to allow an operator using the ultrasonic endoscope 100 to be able to hold the operation portion 109 by hand. The operation portion 109 includes a bending operation mechanism 110, and multiple switches 111. The bending operation mechanism 110 is provided in order to cause the bendable portion 105 to conduct bending motion by pulling the angle wire and to cause the raising stand 108 to conduct motion by pulling the raising wire. The multiple switches 111 are provided in order to perform air feeding, water feeding, and suctioning through the pipe line.

The light source device 113 is a device that emits illumination light so as to perform image-capturing through the optical image-capturing mechanism 103.

The optical observation portion 114 is configured to project a video image captured by the image sensor of the optical image-capturing mechanism 103 on a monitor 116.

The ultrasonic observation portion 115 is configured to receive a signal output from the ultrasonic scanning mechanism 104, to generate an image based on the signal, and to project the image on the monitor 116.

Next, the configuration of the puncture needle 1 will be described.

As shown in FIG. 3, the puncture needle 1 includes an insertion body 2, an operation portion 8, and a stylet 27.

The insertion body 2 is an elongated member which can be inserted through the channel 107 of the ultrasonic endoscope 100 shown in FIG. 1.

As shown in FIG. 4, the insertion body 2 includes the needle tube 3, and the sheath 7 through which the needle tube 3 is inserted.

The needle tube 3 is a cylindrical member having a distal end and a proximal end and is advanced and retracted by the operation portion 8 of the puncture needle 1.

The distal end of the needle tube 3 is sharpened in order to puncture tissue with the needle tube 3. The distal end of the needle tube 3 has an opening 4 for suctioning tissue, inside the needle tube 3.

The opening 4 provided in the distal end of the needle tube 3 is formed by obliquely cutting the distal end of the tubular member forming the needle tube 3, with respect to the tubular member itself and is sharply formed so as to be able to puncture biological tissue. The specific shape of the opening 4 may be appropriately selected from various types of known shapes in consideration of target tissue and the like.

Figure 5:
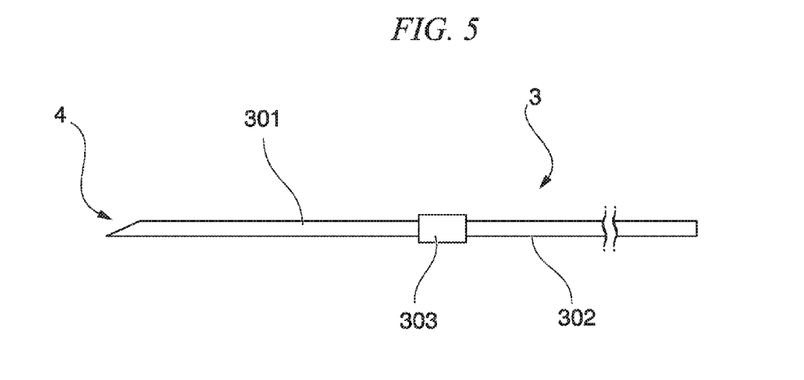
FIG. 5 is a view showing a needle tube of the puncture needle for an endoscope, according to the embodiment of the present invention.

FIG. 5 shows the structure of the needle tube 3. The needle tube 3 is configured to include a distal end region 301 having the opening 4, and a proximal end region 302 configuring the proximal end side of the distal end region 301. The distal end region 301 and the proximal end region 302 are connected to each other by a tubular connection member 303. The distal end region 301 excels in flexibility compared to the proximal end region 302. The proximal end region 302 has bending rigidity higher than that of the distal end region 301 and excels in power transferring properties (pushability) in the longitudinal direction.

As the material of the distal end region 301, for example, a nickel-titanium alloy, a cobalt-chromium alloy, and the like are exemplary examples. As the material of the proximal end region 302, for example, a stainless steel alloy and the like are exemplary examples.

In a case where a cobalt-chromium alloy is employed as the material of the distal end region 301, a bending habit is unlikely to be applied compared to a stainless steel alloy. Accordingly, even if the puncture needle 1 is moved inside the cannel of the treatment tool in the bendable portion that is bent at a small radius of curvature, the bending habit is unlikely to be applied to the distal end region 301 of the needle tube 3. Therefore, the distal end region 301 of the needle tube 3 can straightly punctures the tissue and can easily approach the target tissue.

The connection member 303 is a member having an inner diameter allowing the distal end region 301 and the proximal end region 302 to enter. The needle tube 3 is formed by performing brazing or soldering in a state where the proximal end side of the distal end region 301 and the distal end side of the proximal end region 302 are respectively inserted into the connection member 303 from both sides of the connection member 303.

As shown in FIG. 4, the sheath 7 includes an outer sheath 71 and an inner sheath 74. The above-described needle tube 3 is freely movable forward and rearward inside the inner sheath 74.

The outer sheath 71 includes a coil body 72 and a cylindrical distal end tip 73. The coil body 72 has a configuration in which a metal wire is wound around in a coiled manner. The distal end tip 73 is fixed to the distal end of the coil body 72.

The material and the shape of the wire configuring the coil body 72 are suitably selected by focusing on the flexibility and the restoring force of the coil body 72. For example, the material of the wire is selected from stainless steel, a shape memory alloy, a super-elastic alloy, and the like. The shape of the wire is selected from a shape having a circular cross section, a shape having a rectangular cross section, and the like.

The distal end tip 73 is a cylindrical member that is fixed to the distal end surface of the coil body 72 and in which a penetration hole allowing the needle tube 3 to be inserted therethrough is formed.

The inner sheath 74 is a cylindrical resin member having the distal end and the proximal end. A distal end 74a of the inner sheath 74 is not fixed to the coil body 72 but is fixed to the distal end tip 73. The proximal end (not shown) of the inner sheath 74 extends to the operation portion 109. The distal end 74a of the inner sheath 74 does not have to be fixed to the distal end tip. In such a case, the distal end 74a is freely slidable with respect to the outer sheath 71.

The inner diameter of the distal end tip 73 may be larger than the inner diameter of the inner sheath 74. When the inner diameter of the distal end tip 73 is larger than the inner diameter of the inner sheath 74, the needle tube 3 disposed inside the inner sheath 74 is in a position spaced from the inner surface of the distal end tip 73 in the distal end tip 73, and thus, friction resistance is reduced compared to a case where the needle tube 3 slides with respect to the inner surface of the distal end tip 73.

As shown in FIGS. 1 and 3, the operation portion 8 includes an operation main body 9, an attachment adapter 18, and a needle slider (needle tube operation portion) 23. The attachment adapter 18 is interlocked with the operation main body 9. The needle slider 23 is provided on the proximal end side of the operation main body 9.

The operation main body 9 has a lumen through which the needle tube 3 and the sheath 7 can be inserted. The attachment adapter 18 is attached to the distal end side of the operation main body 9. The proximal end side of the operation main body 9 is inserted into the tubularly formed needle slider 23. The operation main body 9 and the attachment adapter 18, and the operation main body 9 and the needle slider 23 are prevented from relatively rotating around the axial line and are slidable in the axial line direction due to grooves, projection portions, and the like (not shown) which are formed on the outer peripheral surfaces and are engaged with each other.

The attachment adapter 18 is provided in order to adjust the protruding amount of the sheath 7 from the distal end of the channel 107 of the ultrasonic endoscope 100. The attachment adapter 18 is movably interlocked with the operation main body 9 along the longitudinal axis of the attachment adapter 18. The distal end portion of the attachment adapter 18 can be attachable and detachable with respect to the proximal end mouth piece 107b of the ultrasonic endoscope 100.

The needle slider 23 is fixed to the proximal end of the proximal end region 302 of the needle tube 3. The needle slider 23 is interlocked with the operation main body 9 so as to be movable with respect to the longitudinal axis of the operation main body 9.

In the needle tube 3, since the proximal end side of the proximal end region 302 protrudes from the proximal end of the sheath 7 and is fixed to the needle slider 23, the needle tube 3 can project from and retract through the distal end of the sheath 7 by causing the needle slider 23 to slide with respect to the operation main body 9.

As shown in FIG. 3, a stopper 61 restricts the movement of the needle slider 23 Specifically, the needle slider 23 can advance relative to the operation main body 9 to a position where the needle slider 23 comes into contact with the stopper 61. The maximum length protruding from the sheath 7 of the needle tube 3 can be adjusted by adjusting the fixing position of the stopper 61 with respect to the operation main body 9.

A state where the needle slider 23 is at a position in which the needle slider 23 has moved to the end on the proximal end side of the operation main body 9 is the initial state before the puncture needle 1 starts to be used. In other words, the distance between the position of the distal end of the needle slider 23 and the stopper 61 in the initial state becomes the stroke of advancement/retraction of the needle tube 3. In the initial state, the distal end of the needle tube 3 is located inside the sheath 7.

Figure 6:
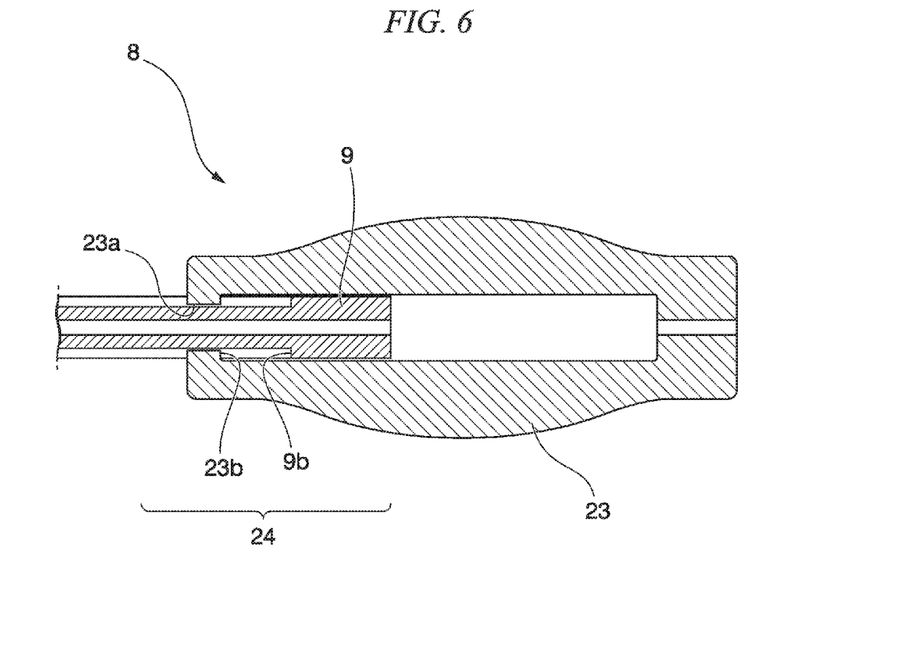
FIG. 6 is a sectional view showing an operation main body and a needle slider of the puncture needle for an endoscope, according to the embodiment of the present invention.

As shown in FIG. 6, the operation main body 9 and the needle slider 23 have a latch structure 24 for restricting the needle slider 23 from moving toward the proximal end side of the operation main body 9. The latch structure 24 is configured to have a latch surface 9b formed in the operation main body 9, and a contact surface 23b formed in a projection portion 23a of the needle slider 23. When the needle slider 23 is moved to the outermost proximal end side relative to the operation main body 9 along the longitudinal axis of the operation main body 9, the latch surface 9b and the contact surface 23b come into contact with each other.

In the initial state where the latch surface 9b and the contact surface 23b are in contact with each other, the needle slider 23 is latched with respect to the operation main body 9.

The stylet 27 is attached to the proximal end surface of the needle slider 23. The stylet 27 is a needle-shaped member that is inserted into the needle tube 3. Without being limited to the needle shape, the distal end of the stylet 27 may have an end surface along a surface intersecting the longitudinal axis of the stylet 27 and may have a curved surface such as a hemisphere surface.

In a state where the puncture needle 1 is mounted in the endoscope 100, the stroke of advancement/retraction of the needle tube 3 is set such that the connection member 303 is positioned between the proximal end of the bendable portion 105 and the proximal end (position 41 centimeters from the distal end of the insertion portion 101) of a follow-bending region R1 (refer to FIG. 1). In other words, when the stopper 61 is maximally advanced with respect to the operation main body 9, at a position where the distal end surface of the needle slider 23 is brought into contact with the stopper 61, the connection member 303 (particularly, the distal end of the connection member 303) is positioned more proximal than the proximal end of the bendable portion 105. In a state where the latch surface 9b of the operation main body 9 and the contact surface 23b of the needle slider 23 are in contact with each other, the connection member 303 (particularly, the proximal end of the connection member 303) is positioned on the distal end side of the proximal end of the follow-bending region R1. Therefore, inside the sheath 7 in the channel 107 that is bent by the bendable portion 105 at a large bending angle, the distal end region 301 of the needle tube 3 is positioned. The proximal end region 302 of the needle tube 3 is positioned inside the sheath 7 in the channel 107 having a substantially linear shape and being more proximal than the proximal end of the follow-bending region R1. In an area between the proximal end of the bendable portion 105 and the proximal end of the follow-bending region R1, in accordance with the stroke of advancement/retraction of the needle tube 3, the distal end region 301 or the proximal end region 302 of the needle tube 3 is positioned. Since the follow-bending region R1 is gently bent compared to the bendable portion 105, the influence with respect to the change in bending rigidity of the needle tube 3 is small. In other words, setting is performed such that the distal end region 301 or the proximal end region 302 passes through the inside of the follow-bending region R1 in accordance with the stroke of advancement/retraction of the needle tube 3. Accordingly, the pushability of the needle tube 3 and the reduction of friction between the inner peripheral surface of the sheath 7 and the outer peripheral surface of the needle tube 3 can be balanced.

As described above, the position of the connection member 303 in the needle tube 3 is set under predetermined conditions such that the connection member 303 is positioned between the proximal end of the bendable portion 105 and the proximal end of the follow-bending region R1.

Figure 7A:
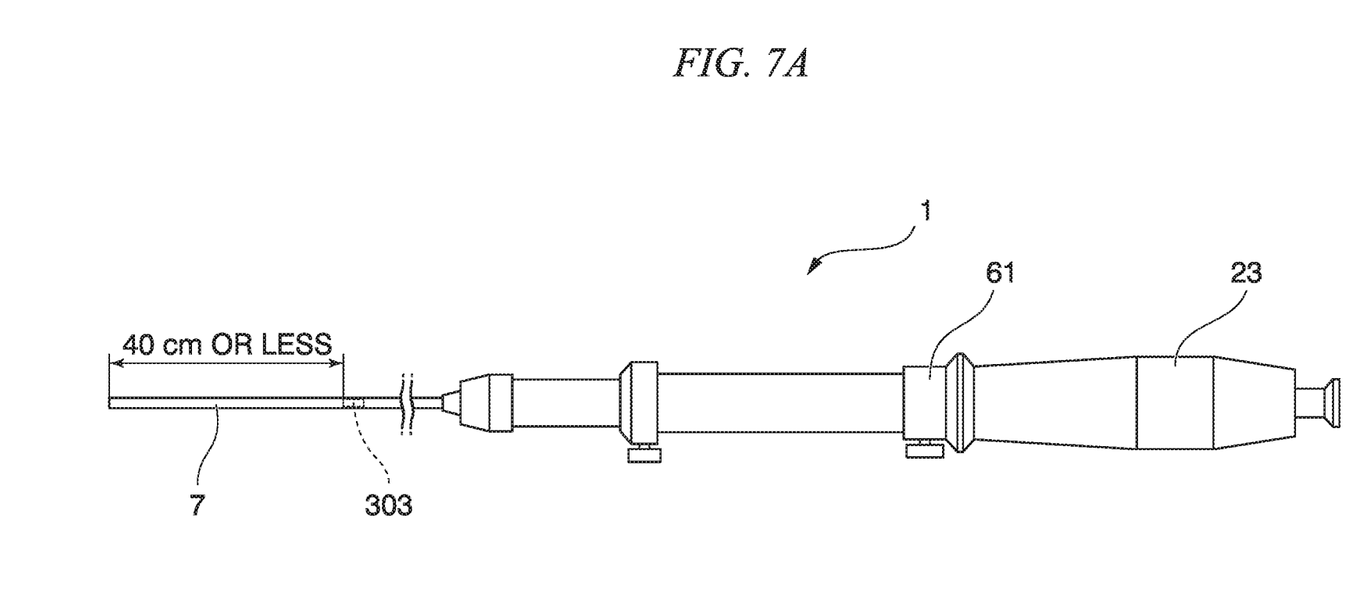
FIG. 7A is a view showing an initial state of the puncture needle for an endoscope, according to the embodiment of the present invention.

In the initial state shown in FIG. 7A, the needle tube 3 is maximally retracted with respect to the sheath 7. In this case, the distal end of the connection member 303 is positioned within a range equal to or less than 40 centimeters from the distal end of the sheath 7.

Figure 7B:
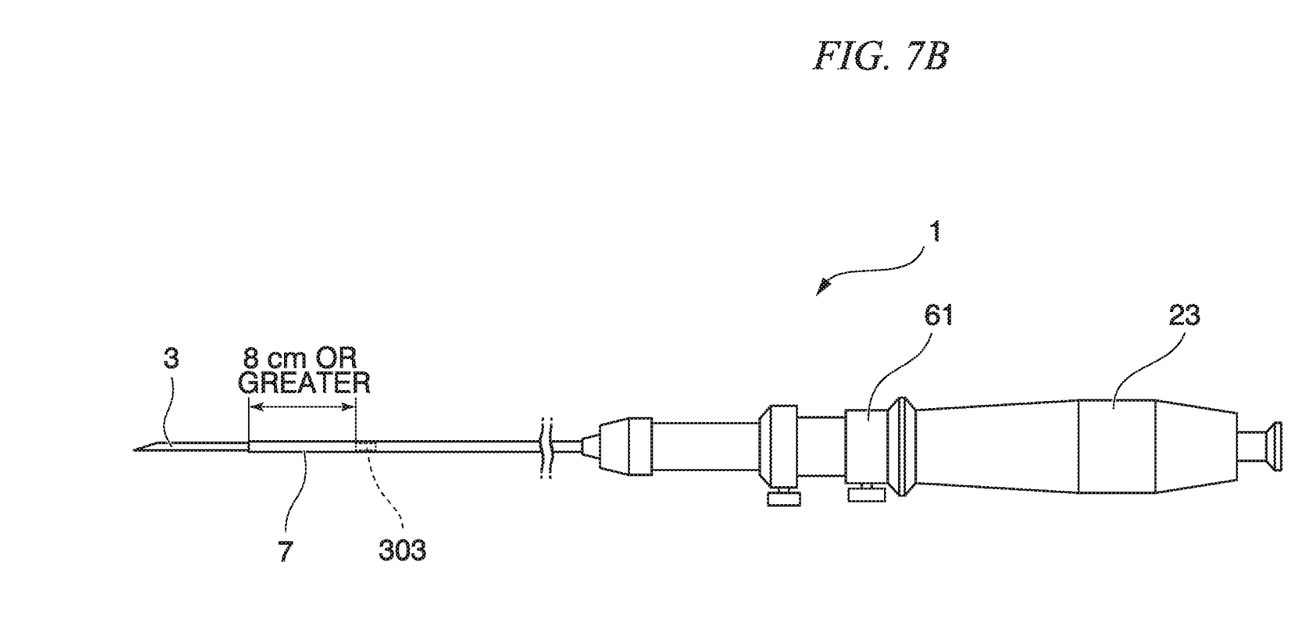
FIG. 7B is a view showing a state where the needle tube of the puncture needle for an endoscope, according to the embodiment of the present invention maximally protrudes.

FIG. 7B shows a state in which the needle tube 3 maximally protrudes by moving the stopper 61 to the end on the distal end side and causing the needle slider 23 to be in contact with the stopper 61. In this case, the distal end of the connection member 303 is positioned within a range equal to or larger than 8 centimeters from the distal end of the sheath 7.

According to the above-described configuration, the connection member 303 which becomes a boundary between the distal end region 301 and the proximal end region 302 in the needle tube 3 moves within only a range of 8 centimeters to 40 centimeters from the distal end of the sheath 7 in response to operation of the needle slider 23. In other words, setting is performed such that none of a case where the proximal end region 302 of the needle tube 3 is positioned within a range less than 8 centimeters from the distal end of the sheath 7, and a case where the distal end region 301 of the needle tube 3 is positioned within a range beyond 40 centimeters from the distal end of the sheath 7 structurally occurs.

An in-use operation of the biopsy system 150 according to the present embodiment having the above-described configuration will be described by applying an example of a case where biopsy is performed with respect to the pancreas head.

First, an operator causes a patient to lie down sideways, inserts the endoscope 100 through the mouth, and introduces the endoscope 100 into the gastrointestinal tract. The operator causes the distal end portion of the endoscope 100 to advance to the duodenal bulb (hereinafter, will be sometimes referred to as "bulb"). Subsequently, the ultrasonic scanning mechanism 104 is brought into contact with a rear wall of the bulb and ultrasonic observation is performed. Then, the positions of the pancreas and the lesion are checked, and a puncture position and the like are specified.

Figure 8:
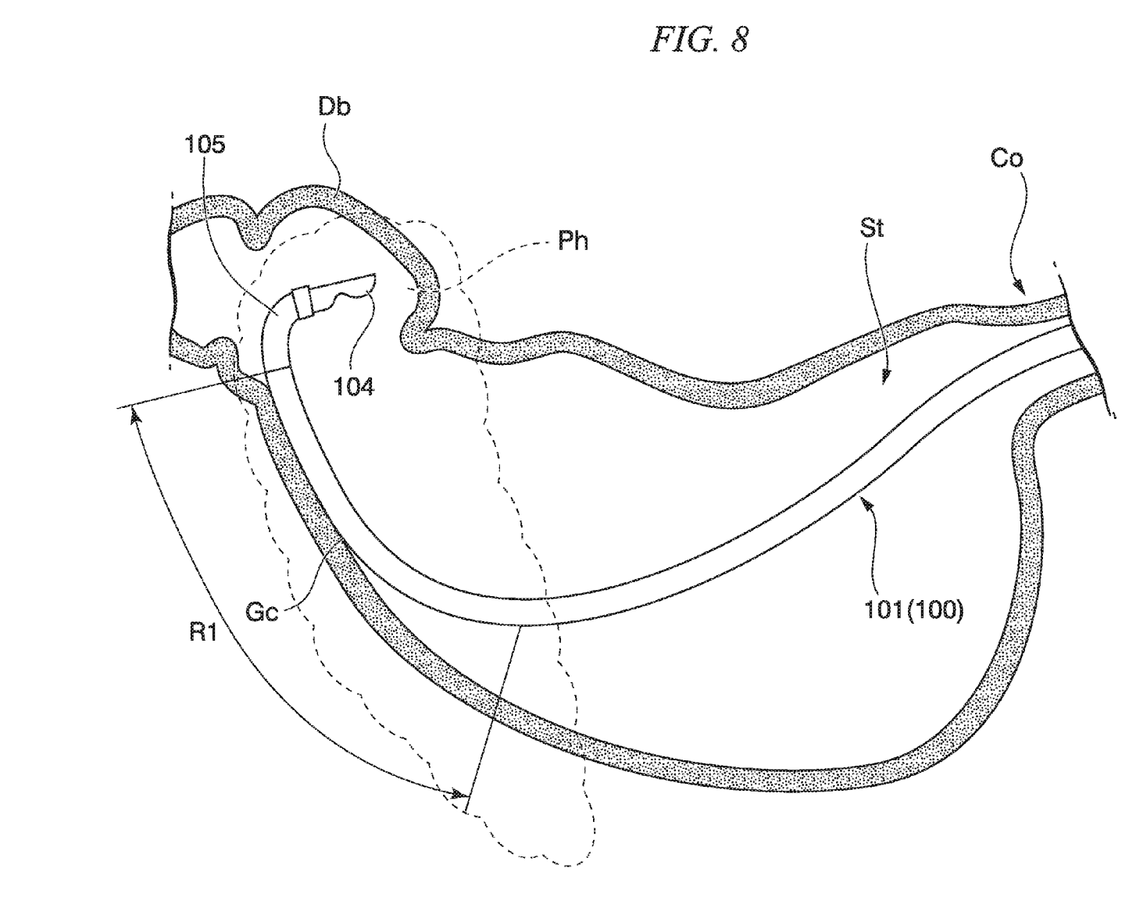
FIG. 8 is a view showing the ultrasonic endoscope in a state where the pancreas head is observed.

FIG. 8 shows the endoscope 100 in a state where the pancreas head is observed. In a case of having access from a duodenal bulb Db to a pancreas head Ph, since the ultrasonic scanning mechanism 104 is brought into contact with the rear wall of the duodenal bulb Db, the bendable portion 105 is bent at a large bending angle. In the insertion portion 101 more proximal than the proximal end of the bendable portion 105, at least a portion of the follow-bending region R1, for example, a region in the vicinity thereof including the position 25 centimeters from the proximal end of the bendable portion 105 is bent so as to come into contact with a greater curvature Gc of a stomach St. In this manner, the follow-bending region R1 denotes a region having a certain length in the insertion portion which can be disposed along the greater curvature Gc in a manner of copying the bending shape of the greater curvature Gc when the distal end portion of the endoscope is positioned in the duodenal bulb Db. In the insertion portion 101, a region more proximal than the proximal end of the follow-bending region R1 extends to a cardiac orifice Co in a substantially linear manner.

The follow-bending region R1 is a portion which is passively bent when external force is received through the greater curvature Gc. Even if external force is received through the greater curvature Gc, in a state where the distal end portion of the endoscope 100 is caused to advance to the duodenal bulb Db, the follow-bending region R1 is in a state having a radius of curvature larger than that of the bendable portion 105.

When the insertion portion 101 has a shape shown in FIG. 8, the region more proximal than the proximal end of the follow-bending region R1 is generally in a substantially linear state and is unlikely to receive force from the stomach walls. Accordingly, the region does not contribute to stabling the position of the ultrasonic scanning mechanism 104 provided in the distal end of the insertion portion 101. Therefore, whether or not the follow-bending region R1 is likely to receive force from the stomach walls at a portion of the greater curvature Gc significantly affects the stability of the position of the ultrasonic scanning mechanism 104 during a technique.

After the puncture position is determined, the operator or an assistant inserts the distal end of the puncture needle 1 in the initial state into the channel 107 of the endoscope 100. When the attachment adapter 18 is fixed to the proximal end mouth piece 107b, the puncture needle 1 is mounted in the endoscope 100. The protruding amount of the sheath 7 from the distal end of the channel 107 in a state where the puncture needle 1 is mounted in the endoscope 100 can be set to a desired length by operating the operation main body 9. Generally, the protruding amount is set to approximately 10 millimeters, for example, to the extent that the distal end of the needle tube 3 protruding from the sheath 7 can be suitable observed by the optical image-capturing mechanism 103.

In a case where the puncture needle 1 is mounted in the endoscope 100 according to the above-described structure of the puncture needle 1 such that the sheath 7 protrudes 10 millimeters from the opening of the distal end of the channel 107, the distal end of the connection member 303 moves within only a range of 7 centimeters to 39 centimeters from the opening of the distal end of the channel 107, that is, within only the range of the follow-bending region R1 in response to operation of the needle slider 23. In other words, in a state where the distal end of the needle slider 23 is brought into contact with the stopper 61, the distal end of the connection member 303 is positioned more proximal than the proximal end of the bendable portion 105. In a state where the contact surface 23b of the needle slider 23 is brought into contact with the latch surface 9b of the operation main body 9, the distal end of the connection member 303 is positioned on the distal end side of the position 39 centimeters from the opening of the distal end of the channel 107.

When the puncture needle 1 is inserted into the channel 107, the insertion portion 101 becomes unlikely to be bent compared to a case before the puncture needle 1 is inserted. However, since the position of the connection member 303 is set as described above in the puncture needle 1, when the endoscope 100 is mounted in the puncture needle 1 in the initial state, only the distal end region 301 in the needle tube 3 is present inside the bendable portion 105. As a result thereof, the puncture needle 1 is unlikely to disturb the bending of the bendable portion 105, and thus, the shape of the bendable portion 105 is suitably retained.

Moreover, since the follow-bending region R1 does not have a linear shape and is in a state of being larger than the radius of curvature of the bendable portion 105, even if any one of the distal end region 301 and the proximal end region 302 is present, flexibility of the follow-bending region R1 is not significantly deteriorated, and the pushability is also unlikely to be deteriorated.

The operator operates the raising stand 108 so as to adjust the orientations of the sheath 7 and the needle tube 3. While the site ahead of the needle tube 3 is checked through an ultrasonic image, the needle slider 23 is moved to the distal end side. Then, the needle tube 3 protruding from the sheath 7 punctures the rear wall of the duodenal bulb Db, penetrates the rear wall, and punctures the pancreas head Ph.

When the needle slider 23 is operated, since the distal end side of the puncture needle 1 (sheath 7) is bent at a bending angle larger than those of the bendable portion 105 and the raising stand 108, high pushability is required in order to move the needle tube 3 forward. In regard to the puncture needle 1, according to the above-described setting, in a state of being mounted in the endoscope 100, only the proximal end region 302 having relatively high bending rigidity is disposed inside the insertion portion 101 in a substantially linear state and at a position more proximal than the follow-bending region R1. Accordingly, high pushability can be retained, and the needle tube 3 can be suitably advanced in response to operation of the needle slider 23. Moreover, when the needle tube 3 is advanced, since only the distal end region 301 which is relatively easy to be bent passes through the inside of the channel 107 bent at a large bending angle, friction resistance due to the bending is reduced, and the needle tube 3 advances without being caught.

After the needle tube 3 punctures tissue of the biopsy target, the stylet 27 is evulsed and suctioning biopsy is performed according to a known procedure.

As described above, in the puncture needle 1 and the biopsy system 150 according to the present embodiment, focusing on the shape of the insertion portion of the endoscope when having access from the duodenal bulb Db to the pancreas, a moving range of the connection member 303 in response to operation of the needle slider 23 is set such that both smooth advancement and retraction and high pushability of the needle tube 3 become compatible regarding the bending shape of the sheath 7 which is bent at a large bending angle. Accordingly, biopsy with respect to the pancreas head requiring a high technology can also be more easily performed than a biopsy system in the related art.

Hereinbefore, the embodiment of the present invention has been described in detail with reference to the drawings. However, the specific configuration is not limited to the embodiment and includes a design change and the like without departing from the scope of the gist of the present invention.

Figure 9:
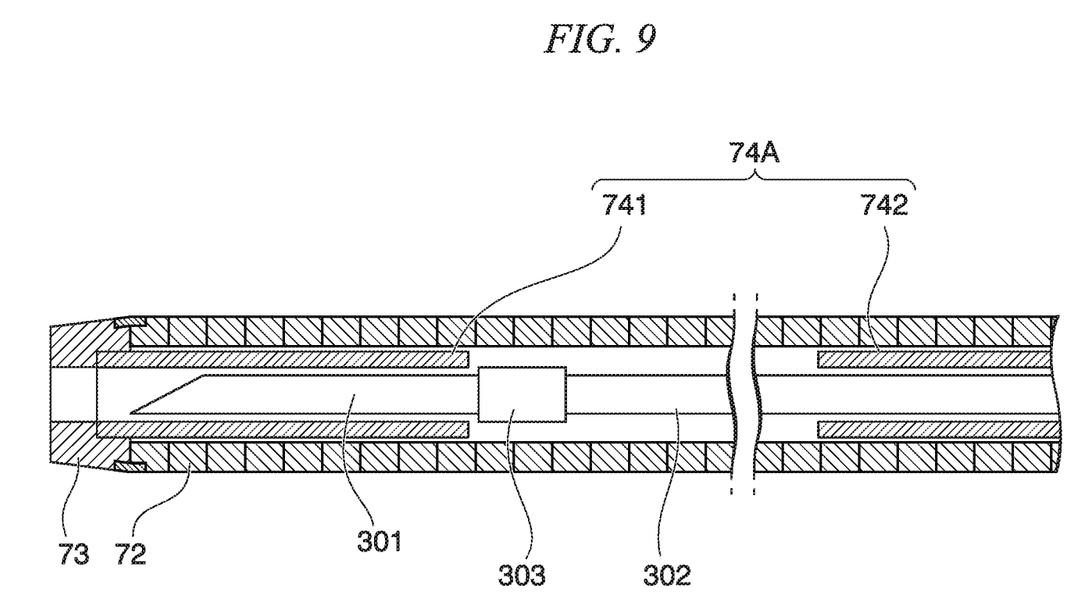
FIG. 9 is a sectional view schematically and partially showing a puncture needle for an endoscope according to a modification example of the present invention.

For example, according to a modification example shown in FIG. 9, an inner sheath 74A may be configured to include a first inner sheath 741 on the distal end side and a second inner sheath 742 on the proximal end side. In such a case, the needle tube 3 disclosed in the first embodiment is freely movable forward and rearward inside the first inner sheath 74 and the second inner sheath 742. The first inner sheath 741 and the second inner sheath 742 are disposed inside the outer sheath 71 while being spaced from each other equal to or larger than the moving range of the connection member 303. The connection member 303 is set so as to advance and retract within only a region between the first inner sheath 741 and the second inner sheath 742 in which none of the inner sheaths is disposed, in response to operation of the needle slider. In other words, in the modification example, the connection member 303 is positioned between the proximal end of the first inner sheath 741 and the distal end of the second inner sheath 742 and is fitted into the first inner sheath and the second inner sheath in an overlapping manner in the radial direction of the first inner sheath and the second inner sheath. In other words, between the proximal end of the first inner sheath 741 and the distal end of the second inner sheath 742, the outer diameter of the connection member 303 is larger than the inner diameters of the first inner sheath 741 and the second inner sheath 742. In this manner, without being restrained by the outer diameter of the connection member 303, the inner diameters of the first inner sheath 741 and the second inner sheath 742 can be set. As a result thereof, while being configured to include the inner sheaths, the puncture needle can also be decreased in diameter.

In the above-described modification example, the first inner sheath 741 and the second inner sheath 742 may be formed of materials different from each other. For example, the first inner sheath 741 may be formed of polyether ether ketone (PEEK) in order to prevent the inner surface from being damaged due to the sharp distal end of the needle tube, and the second inner sheath 742 may be formed of high-density polyethylene (HDPE) in order to reduce sliding resistance with respect to the outer sheath 71 and the needle tube 3. However, in a case where the first inner sheath 741 is formed of polyether ether ketone (PEEK), there is a possibility that rigidity of the distal end portion of the sheath becomes high, thereby resulting in damage to the flexibility. In such a case, the first inner sheath 741 may be formed of two different materials. For example, approximately a range of 2 cm in the distal end of the first inner sheath may be formed of PEEK, and the rear end of the first inner sheath may be formed of HDPE, thereby improving the flexibility. In this manner, in consideration of desired functions, characteristics, and the like intended to be applied, the material for each of the inner sheaths can be selected.

In addition, the lengths and the disposition positions of the first inner sheath and the second inner sheath are not particularly limited as long as the moving range of the connection member is not affected.

Moreover, the second inner sheath may be disposed so as to be slidable with respect to the outer sheath. In this case as well, the puncture needle can be decreased in diameter in a similar manner by causing the inner diameter of the second inner sheath to be less than the outer diameter of the connection member.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A biopsy system comprising:
an endoscope having:
  an insertion portion having:
    a channel; and
    a follow-bending region configured to be passively bent along a greater curvature of a stomach when a distal end of the insertion portion is positioned at a duodenal bulb; and
  a bendable portion provided at a distal end portion of the insertion portion and configured to be bent;
a needle tube which includes a distal end region, and a proximal end region having a higher bending rigidity than a bending rigidity of the distal end region;
a sheath which is configured to be inserted into the channel and has the needle tube inserted therein;
an attachment adapter which is provided on a proximal end side of the sheath and is configured to be mounted to the endoscope; and
a connection member which connects the distal end region and the proximal end region of the needle tube, the connection member being movable in the insertion portion only in a range from a proximal end of the bendable portion to a proximal end of the follow-bending region, in a state where the sheath is inserted through the channel and the attachment adapter is mounted to the endoscope,
wherein only the distal end region of the needle tube is positioned in a region more distal than the proximal end of the bendable portion inside the insertion portion,
at least either of the distal end region and the proximal end region of the needle tube is positioned between a distal end and the proximal end of the follow-bending region inside the insertion portion, and
only the proximal end region of the needle tube is positioned in a region more proximal than the proximal end of the bendable portion inside the insertion portion.

2. The biopsy system according to claim 1,
wherein the proximal end of the follow-bending region is located in a position 41 centimeters from the distal end of the insertion portion.

3. The biopsy system according to claim 1, further comprising:
- a needle tube operation portion which advances and retracts the needle tube relative to the sheath,
- wherein the connection member is movable within the range in accordance with an operation of the needle tube operation portion.

4. The biopsy system according to claim 1, further comprising:
- a treatment tool having:
  - the needle tube;
  - the sheath;
  - a needle tube operation portion which advances and retracts the needle tube relative to the sheath; and
  - the connection member which is movable only in a range from a position 8 centimeters toward a proximal end side of the sheath from a distal end of the sheath to a position 40 centimeters toward the proximal end side of the sheath from the distal end of the sheath in accordance with an operation of the needle tube operation portion.

5. The biopsy system according to claim 4,
wherein the sheath includes a first inner sheath disposed on a distal end side, a second inner sheath disposed more proximal than the first inner sheath and spaced from the first inner sheath, and an outer sheath in which the first inner sheath and the second inner sheath are disposed,
an outer diameter of the connection member is larger than an outer diameter of the distal end region and an outer diameter of the proximal end region of the needle tube, and
the connection member is positioned between a proximal end of the first inner sheath and a distal end of the second inner sheath, and is overlapped with the first inner sheath and the second inner sheath along a radial direction of the first inner sheath and the second inner sheath.

6. A treatment tool comprising:
- a needle tube which includes a distal end region, and a proximal end region having a higher bending rigidity than a bending rigidity of the distal end region;
- a sheath which the needle tube is inserted into;
- a needle tube operation portion which advances and retracts the needle tube relative to the sheath; and
- a connection member which connects the distal end region and the proximal end region of the needle tube,
wherein the sheath includes a first inner sheath disposed on a distal end side, a second inner sheath disposed more proximal than the first inner sheath and spaced from the first inner sheath, and an outer sheath in which the first inner sheath and the second inner sheath are disposed,
an outer diameter of the connection member is larger than an outer diameter of the distal end region and an outer diameter of the proximal end region of the needle tube, and
the connection member is positioned between a proximal end of the first inner sheath and a distal end of the second inner sheath, and is overlapped with the first inner sheath and the second inner sheath along a radial direction of the first inner sheath and the second inner sheath.

7. The treatment tool according to claim 6,
wherein the connection member being movable only in a range from a position 8 centimeters toward a proximal end side of the sheath from a distal end of the sheath to a position 40 centimeters toward the proximal end side of the sheath from the distal end of the sheath in accordance with an operation of the needle tube operation portion.

* * * * *